US008168130B2

(12) United States Patent
Sato et al.

(10) Patent No.: US 8,168,130 B2
(45) Date of Patent: May 1, 2012

(54) PLASMA GENERATION SYSTEM AND PLASMA GENERATION METHOD

(75) Inventors: Takehiko Sato, Sendai (JP); Tatsuyuki Nakatani, Hiroshima (JP); Tatsuo Kimura, Hiroshima (JP)

(73) Assignee: Toyo Advanced Technologies Co., Ltd., Hiroshima (JP)

( * ) Notice: Subject to any disclaimer, the term of this patent is extended or adjusted under 35 U.S.C. 154(b) by 505 days.

(21) Appl. No.: 11/992,007

(22) PCT Filed: Aug. 11, 2006

(86) PCT No.: PCT/JP2006/315958
§ 371 (c)(1),
(2), (4) Date: Mar. 14, 2008

(87) PCT Pub. No.: WO2007/032172
PCT Pub. Date: Mar. 22, 2007

(65) Prior Publication Data
US 2010/0065415 A1 Mar. 18, 2010

(30) Foreign Application Priority Data

Sep. 16, 2005 (JP) .................................. 2005-269989

(51) Int. Cl.
*B01J 19/08* (2006.01)
*A61L 9/00* (2006.01)
*H05H 1/24* (2006.01)
(52) U.S. Cl. ................ 422/186.05; 422/29; 422/186.04; 204/157.15
(58) Field of Classification Search ............. 422/186.01, 422/186.05, 186.04, 29; 204/157.15
See application file for complete search history.

(56) References Cited

U.S. PATENT DOCUMENTS

| | | | | | |
|---|---|---|---|---|---|
| 3,299,299 | A | * | 1/1967 | Dickinson | 310/306 |
| 3,305,466 | A | * | 2/1967 | McCoy | 422/186.05 |
| 3,569,751 | A | * | 3/1971 | Ruhnke | 310/10 |
| 3,674,666 | A | * | 7/1972 | Foster et al. | 422/186.05 |
| 3,742,301 | A | * | 6/1973 | Burris | 361/230 |
| 3,796,857 | A | * | 3/1974 | Henley et al. | 392/315 |
| 4,362,632 | A | * | 12/1982 | Jacob | 422/186.04 |
| 5,316,739 | A | * | 5/1994 | Yoshikawa et al. | 422/186.05 |
| 5,597,456 | A | * | 1/1997 | Maruyama et al. | 204/165 |
| 5,932,116 | A | * | 8/1999 | Matsumoto et al. | 219/121.57 |
| 5,938,854 | A | * | 8/1999 | Roth | 134/1 |
| 6,162,405 | A | * | 12/2000 | Awakowicz et al. | 422/186.05 |
| 6,342,187 | B1 | * | 1/2002 | Jacob et al. | 422/186.05 |

(Continued)

FOREIGN PATENT DOCUMENTS

JP    10-154598    6/1998

(Continued)

OTHER PUBLICATIONS

Translation of Hayashi et al, JP2003-135571.*

(Continued)

*Primary Examiner* — Keith Hendricks
*Assistant Examiner* — Colleen M Raphael

(57) ABSTRACT

A method and system for surely and conveniently generating plasma in a narrow tube having a small diameter.
A first electrode formed by a conductive member covered with an insulator or dielectric is inserted into a narrow tube. The narrow tube is located on a second electrode. A power supply applies an alternating voltage or pulse voltage between the first electrode and the second electrode so that plasma is generated in the narrow tube around the first electrode.

12 Claims, 10 Drawing Sheets

U.S. PATENT DOCUMENTS

| | | | |
|---|---|---|---|
| 6,488,889 B1 * | 12/2002 | Stahlecker et al. | 422/186.05 |
| 7,011,790 B2 * | 3/2006 | Ruan et al. | 422/186.05 |
| 2002/0063537 A1 | 5/2002 | Nam et al. | |
| 2005/0016456 A1 * | 1/2005 | Taguchi et al. | 118/723 E |
| 2006/0042545 A1 * | 3/2006 | Shibata et al. | 118/722 |

FOREIGN PATENT DOCUMENTS

| | | |
|---|---|---|
| JP | 2002-184759 | 6/2002 |
| JP | 2002-184795 | 6/2002 |
| JP | 2003-135571 | 5/2003 |
| JP | 2003-210556 | 7/2003 |
| JP | 2004-527073 | 9/2004 |
| JP | 2004-285187 | 10/2004 |
| JP | 2005-46264 | 2/2006 |
| WO | 02/065820 A1 | 8/2002 |

OTHER PUBLICATIONS

International Search Report (PCT/ISA/210) mailed Oct. 31, 2006 in connection with International Application No. PCT/JP2006/315958.
Japanese Office Action issued on Nov. 16, 2010 in corresponding Japanese Patent Application 2007-535401.

* cited by examiner

| treatment duration [min] | Control | | 1 | | 2 | | 3 | | 4 | | 5 | | 6 | | 10 | | 15 | |
|---|---|---|---|---|---|---|---|---|---|---|---|---|---|---|---|---|---|---|
| Determination | ○ | × | ○ | × | ○ | × | ○ | × | ○ | × | ○ | × | ○ | × | ○ | × | ○ | × |
| Applied voltage 10kV | 0 | 4 | | 2 | 0 | 3 | | 1 | 2 | 4 | 4 | 2 | 2 | 4 | 3 | 0 | | |
| Applied voltage 13kV | 0 | 7 | 0 | 2 | 2 | 0 | 1 | 1 | 3 | 1 | 5 | 0 | 2 | 0 | 3 | 0 | 5 | |

No. 1294

| treatment duration [min] | Control | | 5 | | 10 | | 15 | |
|---|---|---|---|---|---|---|---|---|
| Determination | ○ | × | ○ | × | ○ | × | ○ | × |
| Applied voltage 13kV | 0 | 2 | 1 | 1 | 2 | 0 | 2 | 0 |
| Applied voltage 15kV | | | 2 | | 2 | | | |

PLASMA GENERATION SYSTEM AND PLASMA GENERATION METHOD

CROSS REFERENCE TO RELATED APPLICATIONS

This application claims the benefit under 35 U.S.C. Section 371, of PCT International Application Number PCT/JP2006/315958, filed Aug. 11, 2006, which claimed priority to Japanese Application Number 2005-269989, filed Sep. 16, 2005 in Japan, the contents of which are incorporated herein by reference.

TECHNICAL FIELD

The present invention relates to a plasma generation system and plasma generation method and specifically to a plasma generation system and plasma generation method for generating plasma in a cavity of a narrow tube.

BACKGROUND ART

Using plasma for cleaning, etching, film formation, etc., has been conventionally known.

Patent Document 1 discloses a plasma treatment system for providing stable electric discharge into air without using helium gas, which includes a reaction tube for supplying a reaction gas and first and second electrodes facing each other with the reaction tube located therebetween for acting on the reaction gas. In this system, high frequency power is supplied to the first and second electrodes such that the reaction gas is excited to generate plasma, and a target substrate is treated with the generated plasma.

Patent Document 2 discloses a system for generating uniform discharge plasma under a near-atmospheric pressure irrespective of the type of a gas atmosphere used for treatment. This system includes electrodes facing each other, wherein at least one of the electrodes has a facing surface provided with a solid dielectric, and a pulsed electric field is applied between the electrodes.

The technique disclosed in Patent Document 1 is characterized in that the reaction gas flowing through the reaction tube is converted to plasma which is, in turn, sprayed out of the reaction tube onto a target. The technique disclosed in Patent Document 2 is characterized in that the surface of the target placed on the second electrode plate is treated. Both of these techniques are directed to a surface treatment with the intention that it is carried out with a relatively large device.

On the other hand, using plasma for sterilization and disinfection has been studied. Examples of the conventional medical sterilization actually in practice include high-pressure steam sterilization, ethylene oxide gas sterilization and disinfection as well as peroxide gas sterilization. These have the problems of high temperatures, use of dangerous gas (ethylene oxide gas), unavailability under atmosphere, degassing as long as one week or more, etc. Plasma sterilization systems disclosed in Patent Documents 3 to 5 are directed to sterilization of the cavity of a narrow tube, for which only a few practical sterilization methods have been conceived.

Patent Document 1: Japanese Laid-Open Patent Publication No. 2002-184759
Patent Document 2: Japanese Laid-Open Patent Publication No. 10-154598
Patent Document 3: Japanese Laid-Open Patent Publication No. 2003-135571
Patent Document 4: Japanese Laid-Open Patent Publication No. 2003-210556
Patent Document 5: Japanese Laid-Open Patent Publication No. 2005-46264

DISCLOSURE OF INVENTION

Problems to be Solved by the Invention

The techniques disclosed in Patent Documents 1 and 2 are conceived with the intention that they are carried out with a relatively large device and directed to surface treatment, application of which to sterilization of the cavity of a narrow tube is hence very difficult.

The techniques disclosed in Patent Documents 3 to 5 are directed to a plasma sterilization system for the cavity of a narrow tube. In the technique of Patent Document 3, introduction of gas in a tube is followed by insertion of the plasma generation system into the tube for sterilization. However, the plasma generation system includes a plurality of electrodes and a dielectric base and thus cannot be effectively downsized, so that it cannot be used for sterilization of the cavity of a narrow tube having a diameter of several millimeters or less. In the technique of Patent Document 4, a discharger is inserted into a tube and the inserted discharger is moved. However, the discharger has a needle electrode and a planar electrode and is therefore difficult to insert into a tube having a diameter of several millimeters or less, so that it cannot be used for a narrow tube. In the technique of Patent Document 5, a chemically activated species having a sterilization effect is produced by discharge plasma and is introduced into a tube. Thus, a long tube would lead to attenuation of activity in the midst of the tube, so that the sterilization effect can be lost, or sterilization of the whole tube requires a long period of time.

For treatment of the inner surface of a tube with plasma, the techniques of Patent Documents 1 to 5 cannot be applied to the tube so long as it has a diameter of several millimeters or less for the same reason. Thus, the surface treatment with plasma, such as etching, or the like, of the cavity of the tube having a diameter of several millimeters or less has conventionally been impossible.

The present invention was conceived in view of the above circumstances. An objective of the present invention is to provide a method and device for surely and conveniently generating plasma in the cavity of a tube having a small diameter.

Means for Solving the Problems

To solve the above objectives, a plasma generation system of the present invention is a plasma generation system for generating plasma in a cavity of a narrow tube, including: a first electrode including a conductive member covered with an insulator or dielectric, the first electrode being inserted into the cavity of the narrow tube for generation of the plasma; and a power supply for applying an alternating voltage or pulse voltage to the first electrode. With such a structure, plasma is generated over the surface of the clad made of insulator or dielectric due to discharge, such as dielectric barrier discharge, or the like. The diameter of the conductive member and the thickness of the clad may be adjusted according to the inside diameter of the narrow tube. Even if the inside diameter of the narrow tube is several millimeters or less (e.g., 3 mm or less), plasma can be generated in the cavity of the narrow tube. In view of handleability of the first electrode, the inside diameter of the narrow tube is preferably 0.05 mm or more.

In a preferred embodiment, the plasma generation system further includes a second electrode located outside the narrow tube and connected to the power supply, the power supply applying the alternating voltage or pulse voltage between the first electrode and the second electrode.

In a preferred embodiment, the plasma generation system further includes a ground electrode located outside the narrow tube and connected to the power supply, the power supply applying the alternating voltage or pulse voltage between the first electrode and the ground electrode.

In a preferred embodiment, the plasma generation system further includes a second electrode located in the cavity of the narrow tube and connected to the power supply, the power supply applying the alternating voltage or pulse voltage between the first electrode and the second electrode.

In a preferred embodiment, the plasma generation system further includes a second electrode located in the cavity of the narrow tube, the second electrode being in an electrically floating state.

In a preferred embodiment, the plasma generation system further includes a ground electrode located in the cavity of the narrow tube and connected to the power supply, the power supply applying the alternating voltage or pulse voltage between the first electrode and the ground electrode.

In a preferred embodiment, the plasma generation system further includes a gas supplying member for flowing a gas into the cavity of the narrow tube.

In a preferred embodiment, the plasma generation system further includes a gas remover for removing a gas from the cavity of the narrow tube.

In a preferred embodiment, the plasma is used for a surface treatment on an inner wall of the narrow tube.

In a preferred embodiment, the plasma is used for sterilization of the inner wall of the narrow tube.

The first plasma generation method of the present invention is a plasma generation method for generating plasma in a cavity of a narrow tube, including: an electrode insertion step of inserting into the cavity of the narrow tube a first electrode which includes a conductive member covered with an insulator or dielectric; and a plasma generation step of applying an alternating voltage or pulse voltage to the first electrode to generate plasma in the cavity of the narrow tube.

In a preferred embodiment, the plasma generation step includes generating plasma by applying an alternating voltage or pulse voltage between the first electrode and a second electrode located outside the narrow tube.

In a preferred embodiment, the plasma generation step includes generating plasma by applying an alternating voltage or pulse voltage between the first electrode and a ground electrode located outside the narrow tube.

In a preferred embodiment, the plasma generation step includes generating plasma by applying an alternating voltage or pulse voltage between the first electrode and a second electrode buried in a wall of the narrow tube.

In a preferred embodiment, the plasma generation step includes generating plasma by applying an alternating voltage or pulse voltage between the first electrode and a second electrode located in the cavity of the narrow tube.

In a preferred embodiment, the electrode insertion step includes further inserting a second electrode which is in an electrically floating state into the cavity of the narrow tube.

In a preferred embodiment, the plasma generation step includes generating plasma by applying an alternating voltage or pulse voltage between the first electrode and a ground electrode located in the cavity of the narrow tube.

In a preferred embodiment, the plasma generation step includes flowing a gas into the cavity of the narrow tube.

In a preferred embodiment, the plasma generation method further includes the step of flowing a gas into the cavity of the narrow tube after the plasma generation step.

In a preferred embodiment, the plasma generation method further includes the step of removing a gas from the cavity of the narrow tube after the plasma generation step.

In a preferred embodiment, the plasma generation step includes performing a surface treatment with the plasma on an inner wall of the narrow tube.

In a preferred embodiment, the plasma generation step includes performing sterilization of the cavity of the narrow tube.

The second plasma generation method of the present invention is a plasma generation method for generating plasma in at least one of an outside of a narrow tube and a cavity of the narrow tube, the narrow tube being formed by an insulator or dielectric and including a conductive element in a wall of the tube, the method including: an electrode locating step of locating an electrode outside the narrow tube; and a plasma generation step of applying an alternating voltage or pulse voltage between the electrode and the conductive element to generate plasma in at least one of the outside of the narrow tube and the cavity of the narrow tube.

The third plasma generation method of the present invention is a plasma generation method for generating plasma in a cavity of a narrow tube, the narrow tube being formed by an insulator or dielectric and including a conductive element in a wall of the tube, the method including: an electrode locating step of locating an electrode in a cavity of the narrow tube; and a plasma generation step of applying an alternating voltage or pulse voltage to the conductive element to generate plasma in the cavity of the narrow tube.

The fourth plasma generation method of the present invention is a plasma generation method for generating plasma in a cavity of a narrow tube, the narrow tube being formed by an insulator or dielectric and including a conductive element in a wall of the tube, the method including: an electrode locating step of locating an electrode in a cavity of the narrow tube; and a plasma generation step of applying an alternating voltage or pulse voltage to the electrode to generate plasma in the cavity of the narrow tube.

EFFECTS OF THE INVENTION

The first electrode which has a clad formed by an insulator or dielectric is inserted into a narrow tube to generate plasma. Thus, plasma can be generated even when the inside diameter of the narrow tube is several millimeters or less.

BEST MODE FOR CARRYING OUT THE INVENTION

Hereinafter, embodiments of the present invention will be described in detail with reference to the drawings. Throughout the drawings, elements having substantially the same functions are denoted by the same reference numerals for brevity of illustration.

(Embodiment 1)

A plasma generation system according to embodiment 1 is shown in FIG. 1. The plasma generation system is a system for generating plasma in the cavity of a narrow tube 10. The plasma generation system includes a first electrode 30 which is to be inserted into the cavity of the narrow tube 10 (already inserted in FIG. 1), a second electrode 20 located outside the narrow tube 10, and a power supply 40 for applying an alternating voltage or pulse voltage between the first electrode 30 and the second electrode 20.

The first electrode 30 is formed by, as shown in FIG. 2, a conductive member 31 and a clad 32 of insulator or dielectric covering the surface of the conductive member 31. The conductive member 31 may be made of any conductive material, such as metals, carbon, organic conductive materials, etc. The conductive member 31 of this embodiment is a copper wire.

Examples of the insulator of the clad 32 include fluoric resins, such as PFA, PTFE, FEP, and the like, electrically-insulating polymers, such as polyimide resins, and the like, and electrically-insulating inorganic substances, such as diamond-like carbon (DLC). The dielectric of the clad 32 can be, for example, a material having a high dielectric constant, such as barium titanate, or the like. The clad 32 of this embodiment is made of Teflon®, which is a fluoric resin.

Assuming that the clad 32 is not provided, discharge concentrates at a specific site of the conductive member 31 so that generation of plasma occurs only around the specific site. As a result, there is a high possibility that plasma is not generated throughout the whole cavity of the narrow tube 10 or that the narrow tube 10 is broken by the discharge.

Preferably, the conductive member 31 and the clad 32 are respectively made of materials having high heat resistance, specifically resistant to heat of 50° C. for one hour without degradation, because application of an alternating voltage or pulse voltage between the first electrode 30 and the second electrode 20 such that plasma is generated around the first electrode 30 leads to an increase in temperature of the first electrode 30. In view of the heat resistance, the conductive member 31 is preferably made of a metal, carbon, or the like, and the clad 32 is preferably made of a fluoric resin, polyimide resin, DLC, barium titanate, or the like.

The narrow tube 10 may be made of any material. It should be noted however that, as the narrow tube 10 has a higher insulation property, a higher electric field is applicable between the first electrode 30 and the second electrode 20, so that plasma can be generated more readily.

The second electrode 20 is a ground electrode which is connected to the ground via a ground line 50 and is also connected to the power supply 40 via a connection line 60. The second electrode 20 is not specifically limited to any shape or any material. For example, the second electrode 20 may have a planar shape, cylindrical shape, mesh-like shape, wire shape, etc. The second electrode 20 may be made of any electrically-conductive material, such as a metal, carbon, organic conducting material, or the like. The surface of the second electrode 20 may be covered with an insulator. The second electrode 20 of this embodiment is formed by a metal plate covered with an insulator.

The power supply 40 is designed to apply an alternating voltage or pulse voltage, whose frequency and voltage level are not limited to any particular values because generation of plasma depends on various factors including, for example, the shape, material and length of the first electrode 30, the material and thickness of the narrow tube 10, the distance between the first electrode 30 and the second electrode 20, and the gas species and temperature around the first electrode 30, because they depend on the intensity of plasma, and because the important factor in generation of plasma is not the voltage applied but the intensity of the electric field generated around the first electrode 30. The pulse voltage preferably consists of, as shown in FIG. 3, polarity-varying pulses (from positive (+) to negative (−) or from negative (−) to positive (+)) or pulses rising from 0 V. Chronologically-continuing supply of the pulse voltage advantageously causes continuous generation of plasma. Such a continuously-supplied pulse voltage can also be described as a square-waved alternating voltage.

Although the frequency and voltage level of the power supply 40 are not limited to any particular values, the frequency is preferably 0.1 Hz to 100 MHz in view of practical use as the power supply system and is preferably 50 Hz to 1 MHz in view of readiness of generation of plasma. The voltage is preferably 1 V to 500 kV, at which plasma is readily generated, but is preferably 1 V to 100 kV in view of convenient settings of the system. The intensity of the electric field around the first electrode 30 when the power supply 40 applies an alternating voltage or pulse voltage to the first electrode 30 is preferably between $10^5$ V/m and $10^{10}$ V/m.

Next, a method for generating plasma using the plasma generation system of this embodiment is described.

First, the first electrode 30 in the form of a string is inserted into the narrow tube 10, for example, a catheter. When the narrow tube 10 is made of a flexible material, such as PVC, polyurethane, silicone, Teflon®, or the like, the narrow tube 10 is relatively freely bendable. Since the first electrode 30 is formed by the copper wire (conductive member) 31 and the Teflon® clad 32, the first electrode 30 is inserted into the narrow tube 10 while being bent according to the curvature of the narrow tube 10.

After the first electrode 30 is inserted throughout a region in which plasma is to be generated, the narrow tube 10 including the first electrode 30 inserted therethrough is placed on the second electrode 20. The narrow tube 10 may be in a straight form lying on the second electrode 20 as shown in FIG. 1 but may be, if the narrow tube 10 is long as compared with the size (area) of the second electrode 20, in a curved form lying on the second electrode 20.

Then, an alternating voltage or pulse voltage is applied between the first electrode 30 and the second electrode 20 to generate plasma. When the narrow tube 10 is in a straight form lying on the second electrode 20, the distance between the first electrode 30 and the second electrode 20 is substantially constant across the length of the first electrode 30 over the second electrode 20. When the narrow tube 10 is in a curved form lying on the second electrode 20, the distance between the first electrode 30 and the second electrode 20 is also substantially constant across the length of the first electrode 30 over the second electrode 20. Accordingly, the intensity of an electric field generated is substantially constant across the length of the first electrode 30. Therefore, plasma is generated substantially uniformly across the length of the first electrode 30. How much the plasma is generated can be determined from the degree of emission around the first electrode 30 or the discharged current per unit length across the length of the first electrode 30. The degree of emission of plasma can readily be confirmed by eyes if the narrow tube 10 is transparent. In this case, even if the narrow tube 10 is not transparent, emission from the plasma can be confirmed by eyes so long as the narrow tube 10 transmits several percents of the emission.

Since in this embodiment, as described above, the first electrode 30 which includes the conductive member 31 covered with an insulator or dielectric is inserted into the cavity of the narrow tube 10 and an alternating voltage or pulse voltage is applied to the first electrode 30 to generate plasma, the plasma can be generated in the cavity of the narrow tube 10, even when the inside diameter of the narrow tube 10 is rendered smaller, by downsizing or thinning the first electrode 30. Where for example the conductive member 31 is a copper wire of 0.08 mm and the clad 32 is a Teflon® layer having a thickness of 0.01 mm, the first electrode 30 can be inserted into the narrow tube 10 so long as the narrow tube 10 has an inside diameter greater than 0.1 mm. It is very difficult to insert the plasma generation system of Patent Document 4 into the narrow tube 10 having such a small inside diameter. In this embodiment, plasma is generated around the whole of the first electrode 30, the whole cavity of the narrow tube 10 can be treated with plasma at a time so that the plasma treatment can be completed within a short period of time. The plasma generation system of this embodiment has a very simple structure, and therefore, the production cost thereof is low. Also, the plasma can easily be generated using the plasma generation system of this embodiment even by an unskilled person.

In the plasma generation system of this embodiment, to generate plasma substantially uniformly across the length of the first electrode 30 on a continuous basis, it is conceivable to position the leading end of the first electrode 30 far away from the second electrode 20 or to form the leading end of the first electrode 30 such that the clad 32 of the leading end of the first electrode 30 has a greater thickness than the other portion of the first electrode 30 or that the leading end of the first electrode 30 is made of a material having higher insulation property or dielectricity than the other portion of the first electrode 30. The former option can readily be applicable if the opposite ends of the narrow tube 10 respectively have openings.

In the other portion of the first electrode 30 than the leading end, non-uniformity of the plasma generation intensity does not matter to some purposes of plasma treatment. Therefore, generation of plasma may not be uniform across the length of the first electrode 30. Namely, generation of plasma may be irregular or plasma generation intensity may be nonuniform across the length of the first electrode 30.

(Embodiment 2)

A plasma generation system of embodiment 2 includes, as shown in FIG. 4, a gas supplier 80 in addition to the components of the plasma generation system of embodiment 1. The plasma generation system and plasma generation method of embodiment 2 are substantially the same as those of embodiment 1, and the differences of embodiment 2 from embodiment 1 are mainly described below.

In this embodiment, an opening of the narrow tube 10 through which the first electrode 30 is to be inserted is provided with an adapter 70 which allows introduction of a predetermined gas from the gas supplier 80 into the cavity of the narrow tube 10. The adapter 70 and the gas supplier 80 are connected to each other by a pipe. An example of the gas supplier 80 is a compressed gas chamber with a pressure reduction valve. The predetermined gas refers to a gas selected from among a variety of gasses in view of the purpose of generation of plasma. For example, introduction of Ar or He into the cavity of the narrow tube 10 allows plasma to be generated more readily than in the atmosphere. Introduction of oxygen results in generation of ozone or oxygen radicals. For example, specific organic molecules can be coupled to the inner wall of the narrow tube 10 by introducing a gas which contains the organic molecules. Alternatively, the inner wall of the narrow tube 10 can be coated with a resin by introducing a gas which includes monomers.

Next, a method for generating plasma using the plasma generation system of this embodiment is described.

First, the adapter 70 is attached to the opening of the narrow tube 10. On the other hand, the adapter 70 is connected to the gas supplier 80. The first electrode 30 is inserted into the cavity of the narrow tube 10 through the adapter 70. Then, the narrow tube 10 is placed on the second electrode 20.

Then, the predetermined gas is supplied from the gas supplier 80 into the cavity of the narrow tube 10, and an alternating voltage or pulse voltage is applied between the first electrode 30 and the second electrode 20 to generate plasma. The gas may be supplied all the time during application of the voltage. Alternatively, introduction of the gas into the cavity and stoppage of the introduction of the gas may be followed by application of the voltage. When the end of the narrow tube 10 opposite to the adapter 70 has an opening, it is preferable that the gas is continuously supplied during the application of voltage.

After the generation of plasma, a gas of the same type as or different type from the gas supplied during the generation of plasma is flowed into the cavity of the narrow tube 10, such that part of the gas supplied during the generation of plasma and remaining in the cavity and a gas or species chemically changed by plasma are entirely exhausted from the narrow tube 10. It should be noted that this step is unnecessary if the gas exhaustion is unnecessary.

At the first step, the first electrode 30 may be inserted into the cavity of the narrow tube 10 before the adapter 70 is attached to the opening of the narrow tube 10.

This embodiment has, in addition to the effects of embodiment 1, the advantage of achieving more effective treatment according to the purposes of the plasma treatment because of introduceability of any type of gas into the cavity. For example, sterilization with ozone or other active species can be carried out with a low voltage within a short period of time; the inner wall of the narrow tube 10 can be etched uniformly over the entire inner wall within a short period of time; an active group can be chemically bonded to the inner wall of the narrow tube 10; or the inner wall can be coated. Since active species or harmful gas remaining in the narrow tube 10 after the plasma treatment can be quickly removed by flowing another gas into the narrow tube 10, the plasma treatment can be carried out to leave no internal contamination.

Next, sterilization with plasma and surface treatment with plasma are described with reference to examples which use the plasma treatment system of this embodiment.

EXAMPLE 1

The first electrode formed by a copper wire having a diameter of 0.254 mm and a Teflon® clad was inserted into the cavity of a PVC narrow tube having an outside diameter of 5 mm, inside diameter of 3 mm and length of 1 m, and an alternating voltage was applied to the first electrode to sterilize the inside of the narrow tube. Both ends of the narrow tube were sealed. The power supply used was an AC power supply of a sine wave at 6 kHz. Herein, the magnitude of the voltage applied is a peak-to-peak representation.

Results of plasma irradiation with varying voltage magnitudes and treatment durations (voltage application times) are shown in FIG. 5. Determination as to whether sterilization was successful or not was carried out using ATTEST290 and 290G available from 3M Company. The numbers shown with the upper and lower tables of FIG. 5, No. 1291 and No. 1294, refer to the numbers of the bioindicators used for the determination. The determination as to whether sterilization was successful or not was carried out based on whether or not the number of bacteria was decreased by a factor of 100,000 or more by plasma treatment. Namely, if the number of bacteria was decreased by a factor of 100,000 or more by plasma treatment, it was determined that sterilization was successful ("O" in the tables). If not, it was determined that sterilization failed ("x" in the tables). The numerical values shown in the tables each refer to the number of determination of success "O" or failure "x" (i.e., the number of trials). It should be noted that "Control" means no plasma treatment performed.

As seen from the upper table of FIG. 5, the plasma treatment with applied voltage of 13 kV for the treatment duration of 5 minutes resulted in 5 successes out of 5 trials. With applied voltage of 10 kV, not all of more than one trials of sterilization succeeded when the treatment duration was shorter than 10 minutes. Also, as seen from the results shown in the lower table of FIG. 5, application of voltage of 15 kV achieves sterilizability at least equivalent to that achieved by application of voltage of 13 kV. In comparison to conventional ethylene oxide gas sterilization systems and hydrogen peroxide gas sterilization systems which require several hours or more before completion of sterilization and one week for degassing of ethylene oxide gas, sterilization by the method of this embodiment is incommensurably quick.

EXAMPLE 2

The first electrode formed by a copper wire having a diameter of 0.018 mm and a Teflon® clad was inserted into the cavity of a polyurethane narrow tube having an outside diameter of 0.7 mm, inside diameter of 0.5 mm and length of 48 mm, and an alternating voltage was applied to the first electrode to perform a surface treatment (etching) on the inner wall of the narrow tube. Both ends of the narrow tube were open. The power supply used was an AC power supply of a sine wave at 6 kHz. Herein, the voltage applied was 8 kV.

FIG. 10 shows a laser microscopic image (×3,000) of the inner wall of the narrow tube to which a voltage was applied for 2 minutes. For comparison, a laser microscopic image (×3,000) of the inner wall of the (untreated) narrow tube which was not plasma-treated is shown in FIG. 11. It is found that the untreated inner wall has small irregularities while the plasma-treated inner wall has no such irregularities because they were etched away from the inner wall by the plasma treatment.

(Embodiment 3)

A plasma generation system of embodiment 3 uses a conductive member buried in a narrow tube to generate plasma.

The narrow tube 11 used in this embodiment includes a conductive element 22 in the wall as shown in FIG. 6. The narrow tube 11 is formed by an insulator or dielectric. An example of the narrow tube 11 is a type of catheter. The narrow tube 11 of this embodiment is made of polyurethane, and the conductive element 22 is made of a copper wire.

The plasma generation system of this embodiment includes, as shown in FIG. 7, a power supply 40 and an electrode 20 provided outside the narrow tube 11. It should be noted that the conductive element 22 buried in the narrow tube 11 can be referred to as the first electrode while the electrode 20 provided outside the narrow tube 11 can be referred to as the second electrode. The electrode (second electrode) 20 and power supply 40 used herein are the same as those of embodiment 1, and therefore, the descriptions thereof are herein omitted.

In this embodiment, the narrow tube 11 is first placed on the electrode 20. This means that the electrode 20 is provided outside the narrow tube 11. Then, the conductive element 22 and the power supply 40 are connected together and the electrode 20 and the power supply 40 are connected to each other via a connection line 60. In this embodiment, the electrode 20 is not connected to the ground. It should be noted that these connections may be established before the narrow tube 11 is placed on the electrode 20.

Then, the power supply 40 applies an alternating voltage or pulse voltage between the conductive element 22 and the electrode 20. This application of voltage leads to generation of plasma in at least one of the outside of the narrow tube 11 and the cavity of the narrow tube 11 around the conductive element 22. The place of generation of the plasma depends on the relative physical relationship between the conductive element 22 and the electrode 20. For example, if the conductive element 22 is positioned to face the electrode 20 with the cavity therebetween, plasma is generated mainly in the cavity but is not substantially generated outside the narrow tube 11. Such generation of plasma realizes sterilization or surface treatment (roughening, coating, hydrophilization, etc.) on at least one of the inner and outer walls of the narrow tube 11.

Since in this embodiment the conductive element 22 buried in the narrow tube 11 is used to generate plasma, the structure of the plasma generation system itself is simple, and plasma can readily be generated. Further, plasma can be generated in the cavity irrespective of the size of the cavity. Therefore, a plasma treatment can be carried out on the cavity of a very small diameter.

(Embodiment 4)

A plasma generation system of embodiment 4 shown in FIG. 9 includes a gas remover 90 in addition to the components of the plasma generation system of embodiment 2. Since the components other than the gas remover 90 are the same as those of embodiment 2, only the differences from embodiment 2 are herein described.

The gas remover 90 is connected to the adapter 70 via a pipe. In this embodiment, after sterilization or surface treatment is performed on the cavity of the narrow tube 10 by means of generation of plasma, gas or active species remaining in the cavity is removed by the gas remover 90. An example of the gas remover 90 is a vacuum pump, which preferably quickly removes gas or active species remaining in the narrow tube 10 or adsorbed on the inner wall of the narrow tube 10. In this case, an end of the narrow tube 10 opposite to the end to which the adapter 70 is attached is preferably closed.

It should be noted that the gas remover 90 may be used before generation of plasma. For example, to perform a plasma treatment in a specific gas atmosphere, the cavity of the narrow tube 10 can be degassed in advance by the gas remover 90 before the specific gas is introduced from the gas supplier 80 for the plasma treatment. With this, a specific plasma treatment can surely be performed without causing another spin-off process.

This embodiment possesses, in addition to the advantages of embodiment 2, the advantage of quickly and entirely removing gas or active species remaining in the cavity after a plasma treatment in an easy fashion and the advantage of cleaning the cavity before a plasma treatment.

(Embodiment 5)

A plasma generation system of embodiment 5 is the same as the plasma generation system of embodiment 1 except for a connection between the power supply and the second electrode, and therefore, only the differences from embodiment 1 are herein described.

In this embodiment, as shown in FIG. 8, the second electrode 20 is only connected to the ground but is not directly connected to the power supply 40. However, the power supply 40 is also connected to the ground via a ground electrode 65 and, therefore, it can be said that the second electrode 20 and the power supply 40 are indirectly connected to each other via the ground. In an alternative arrangement of this embodiment, both the second electrode 20 and the power supply 40 may be substantially grounded without using an optional ground electrode. An example of this alternative arrangement is that the power supply 40 is connected to the outer wall of the plasma generation system and is also connected to a floor to which the outer wall of the plasma generation system is grounded.

This embodiment possesses the same advantages as those of embodiment 1.

(Embodiment 6)

A plasma generation system of embodiment 6 is substantially the same as that of embodiment 4 except for the structure of the second electrode, and therefore, the descriptions presented herein are focused on the differences from embodiment 4.

In this embodiment, as shown in FIG. 12 and FIG. 13, the second electrode 132 is formed by a conductive member 102 in the form of a wire and a clad 105 of an insulator or dielectric, which is the same as the structure of a first electrode 131 formed by a conductive member 101 in the form of a wire and the clad 105. The first electrode 131 and the second electrode 132 are in parallel to each other and integrally covered with the clad 105 such that the parallel relationship is fixed to form a parallel electrode pair cable 100. Thus, the electrodes are maintained parallel to each other even when the first electrode 131 is inserted into the cavity of the narrow tube 10. It should be noted that the materials and structures of the conductive members 101 and 102 and clad 105 of the electrodes 131 and 132 are the same as those of the first electrode 30 of embodiment 1.

In comparison to embodiments 1 to 5, the second electrode 132 is inserted together with the first electrode 131 into the cavity of the narrow tube 10 and is connected to the power supply 40 before an alternating voltage or pulse voltage is applied between the second electrode 132 and the first electrode 131. The alternating voltage or pulse voltage applied herein is the same as that described in embodiment 1.

In this embodiment, the second electrode 132 which is a covered electric line is positioned substantially in parallel to the first electrode 131 which is another covered electric line to form the parallel electrode pair cable 100 and is integrally inserted as the parallel electrode pair cable 100 into the narrow tube 10 before an alternating voltage or pulse voltage is applied between the electrodes 131 and 132. Therefore, plasma can readily be generated in the narrow tube 10 as in embodiment 1. Further, this embodiment enables the plasma treatment (surface treatment or sterilization) as described in embodiment 4 in the same way and possesses the same advantages.

It should be noted that part of the clad 105 at the tip of the first electrode 131 preferably has a greater thickness or is made of a material having higher insulating property or dielectricity than the other part such that generation of plasma does not concentrate at the tip of the first electrode 131. With such an arrangement, plasma can be generated substantially uniformly across the length of the first electrode 131.

(Embodiment 7)

A plasma generation system of embodiment 7 is substantially the same as that of embodiment 6 except for the connection between the second electrode 132 and the power supply 40, and therefore, the descriptions presented herein are focused on the differences from embodiment 6.

In this embodiment, as shown in FIG. 14, part of the second electrode 132 residing in the narrow tube 10 constitutes a portion of the parallel electrode pair cable 100 extending parallel to the first electrode 131 as does in embodiment 6 but the other part of the second electrode 132 outside the narrow tube 10 and the adapter 70 is separated from the first electrode 131. A second electrode connecting portion 132' at the tip of the separated part is connected to the ground. Meanwhile, the power supply 40 is also connected to the ground.

The plasma generation system of this embodiment can perform the same plasma treatment as that of embodiment 6 in the same way and possesses the same advantages.

(Embodiment 8)

A plasma generation system of embodiment 8 is substantially the same as that of embodiment 7 except that the second electrode 132 is not connected to the ground, and therefore, the descriptions presented herein are focused on the differences from embodiment 7.

In this embodiment, as shown in FIG. 15, part of the second electrode 132 residing in the narrow tube 10 constitutes a portion of the parallel electrode pair cable 100 extending parallel to the first electrode 131 as does in embodiment 6 but the other part of the second electrode 132 outside the narrow tube 10 and the adapter 70 is separated from the first electrode 131. A second electrode connecting portion 132' at the tip of the separated part is connected to none of the power supply 40, the first electrode 131 and the ground to be in an electrically floating state. Meanwhile, the power supply 40 is connected to the ground. Even if the second electrode 132 is in an electrically floating state, plasma is generated around the first electrode 131 inserted in the narrow tube 10.

The plasma generation system of this embodiment can perform the same plasma treatment as that of embodiment 7 in the same way and possesses the same advantages.

(Embodiment 9)

A plasma generation system of embodiment 9 is substantially the same as that of embodiment 6 except for the structure of the second electrode, and therefore, the descriptions presented herein are focused on the differences from embodiment 6.

In this embodiment, as shown in FIG. 16 and FIG. 17, a second electrode 133 is formed by a bare conductive member which is not covered. Examples of the material of this conductive member include metals, carbon, organic conductive materials, etc.

The second electrode 133 is adhered onto the outer surface of the clad 105 of the first electrode 131 and extends substantially parallel to the first electrode 131. The second electrode 133 is combined with the first electrode 131 to form a parallel electrode pair cable 109 inside and outside the narrow tube 10 as in embodiment 6 and is connected to the power supply 40, and an alternating voltage or pulse voltage is applied between the second electrode 133 and the first electrode 131. The alternating voltage or pulse voltage applied herein is the same as that described in embodiment 1.

The plasma generation system of this embodiment can perform the same plasma treatment as that of embodiment 6 in the same way and possesses the same advantages.

(Embodiment 10)

A plasma generation system of embodiment 10 is substantially the same as that of embodiment 3 except that the structure of the second electrode is different and that the system of embodiment 10 includes a gas supplier and gas remover, and therefore, the descriptions presented herein are focused on the differences from embodiment 3.

The plasma generation system of this embodiment includes the conductive element 22 buried in the wall of the narrow tube 11 as shown in FIG. 6 and an electrode 134 formed by a conductive member in the form of a wire covered with an insulator or dielectric, which is to be inserted into the cavity of the narrow tube 11 as shown in FIG. 18. The conductive element 22 and the electrode 134 are connected to the power supply 40. As in embodiment 1, an alternating voltage or pulse voltage is applied between the conductive element 22 and the electrode 134. The power supply 40 is connected to the ground, and the electrode 134 is connected to a ground line. When an alternating voltage or pulse voltage is applied, plasma is generated around the conductive element 22. Herein, a larger amount of plasma is generated inside the narrow tube 11 because the electrode 134 is located in the cavity of the narrow tube 11.

The gas supplier 80 of this embodiment is the same as that described in embodiment 2, and the gas remover 90 of this embodiment is the same as that described in embodiment 4. Thus, the plasma generation system of this embodiment can perform the same plasma treatment as that of embodiment 4 in the same way and possesses the same advantages. The plasma generation system of this embodiment also possesses the advantages of embodiment 3.

(Other Embodiments)

The above-described embodiments are examples of the present invention, and the present invention is not limited to these examples. For example, the shape of the conductive member of the first electrode is not limited to a wire shape but may be any shape, such as a planar shape, a film shape, or the like.

In embodiments 1, 2, 4 and 5, the narrow tube may be made of a conductive material (e.g., metal). In this case, it is not necessary to provide the second electrode outside the narrow tube. Plasma can be generated by, for example, connecting the narrow tube to the ground or to the power supply.

The discharge which occurs at the first electrode is not limited to any specific example but may be dielectric barrier discharge, glow discharge, corona discharge, or the like. Any form of discharge can be employed so long as plasma is generated.

The systems of embodiments 3 and 5 may have a gas supply and/or gas remover as in embodiments 2 and 4, such that a certain type of gas can be supplied for plasma treatment.

In embodiments 1 to 4, the second electrode may not be connected to the power supply 40.

In embodiments 1 to 3, the second electrode may not be connected to the ground.

The specifications of the narrow tube, e.g., shape, diameters, length, material, etc., are non-limiting. The cross-sectional shape of the outer wall or cavity of the narrow tube is not limited to circular but may be polygonal, oval, or any other shape. The shape and/or diameter of the narrow tube may be non-uniform across the length of the narrow tube. One end or both ends of the narrow tube may be closed.

In any of the above embodiments, the leading end of the first electrode may be positioned inside the narrow tube or may be positioned outside the narrow tube. In embodiments 6 to 10, the leading end of each of the second electrodes 132 and 133 and the electrode 134 may be positioned inside the narrow tube or may be positioned outside the narrow tube.

In embodiments 6 to 10, at least one of the gas supplier 80 and the gas remover 90 may not be provided.

In any of embodiments 6 to 8, the second electrode may not be covered.

In embodiment 10, the electrode 134 may not be connected to the power supply 40 but to the ground or may be in an electrically floating state. The electrode 134 may be formed by a bare conductive member which is not covered. An alternating voltage or pulse voltage may be applied to the electrode 134 while the conductive element 22 is not connected to the power supply 40 but connected to the ground or electrically floating because in this case plasma is also generated.

The plasma generation system may further include an insertion element for inserting the first electrode or parallel electrode pair cable into the narrow tube. The insertion element preferably has the function of flexibly adjusting the direction of the first electrode or parallel electrode pair cable that is to be inserted even if the narrow tube has a curvature.

In embodiments 6 to 9, the first electrode and second electrode may be separated from each other. In this case, the system may further include a distance adjuster for adjusting the distance between the first electrode and the second electrode. Adjustability of the distance between the two electrodes at any positions enables flexible adjustment of the location of generation of plasma.

In any of the above embodiments, connection of the power supply to the ground is arbitrary. When the power supply is connected to the ground, the second electrode (if present) is preferably connected to the ground side of the power supply, though the connection of the second electrode is not limited to this arrangement.

Industrial Applicability

As described above, a plasma generation device and plasma generation method according to the present invention enable easy generation of plasma in a narrow tube and are useful for sterilization of the cavity of a narrow tube, surface treatment on the inner wall of a narrow tube, etc.

BRIEF DESCRIPTION OF DRAWINGS

FIG. 5 shows the results of sterilization test of Example 1.

DESCRIPTION OF REFERENCE NUMBERS

Figure 1:
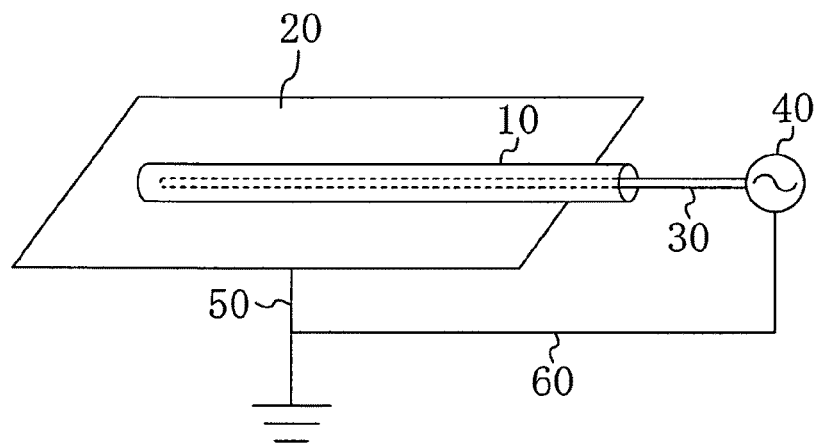
FIG. 1 is a schematic perspective view of a plasma generation system according to embodiment 1.
Figure 2:
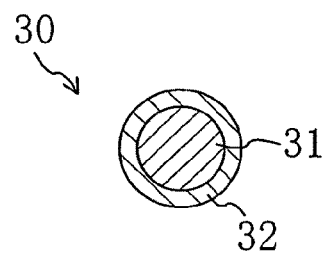
FIG. 2 is a cross-sectional view of the first electrode.
Figure 3:
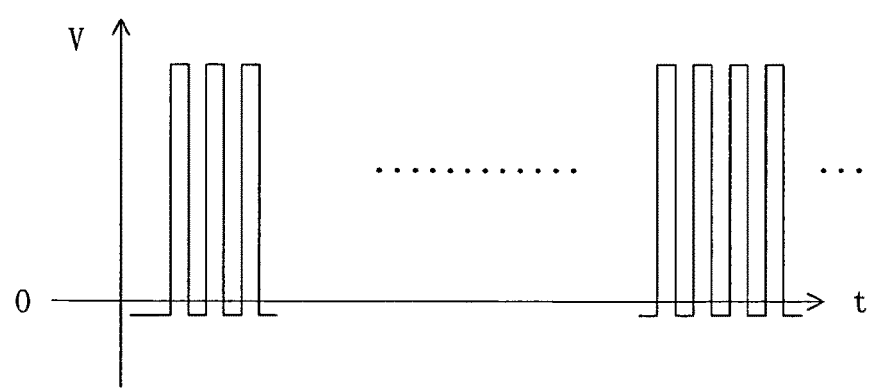
FIG. 3 shows a pulse voltage.
Figure 4:
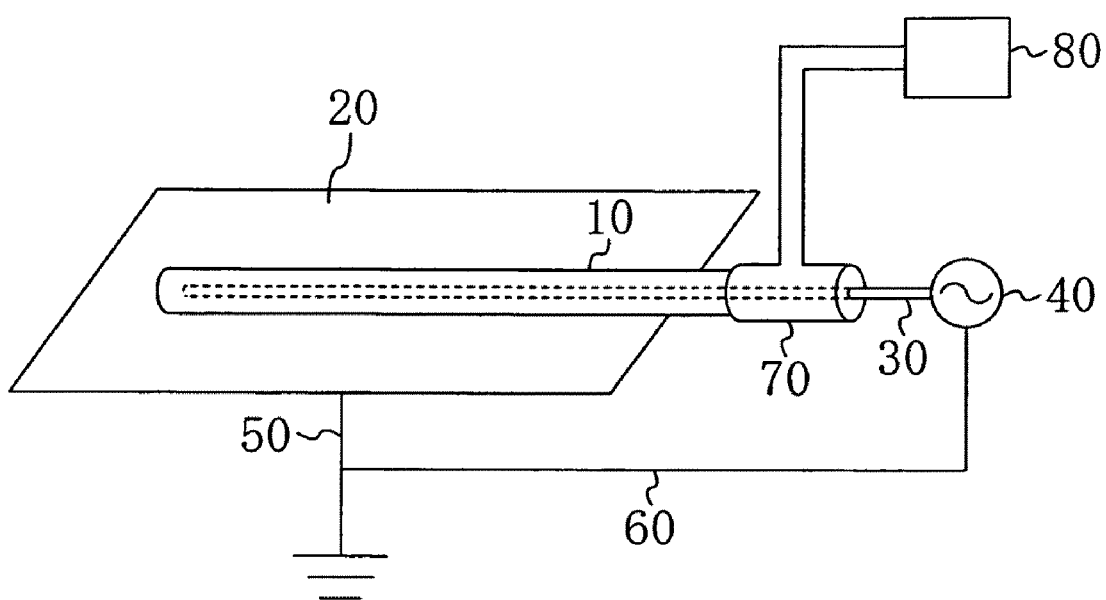
FIG. 4 is a schematic perspective view of a plasma generation system according to embodiment 2.
Figure 6:
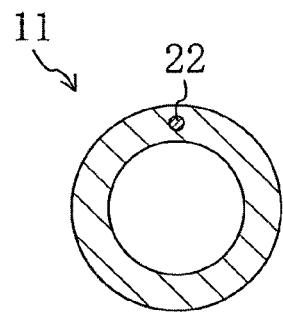
FIG. 6 is a cross-sectional view of a narrow tube according to embodiment 3.
Figure 7:
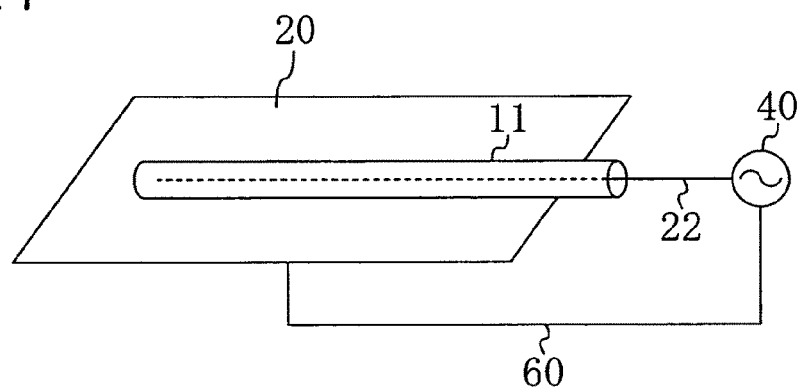
FIG. 7 is a schematic perspective view of a plasma generation system according to embodiment 3.
Figure 8:
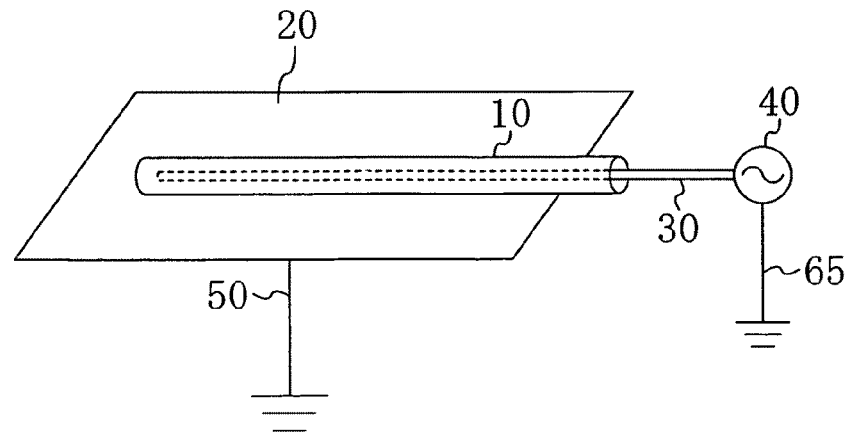
FIG. 8 is a schematic perspective view of a plasma generation system according to embodiment 5.
Figure 9:
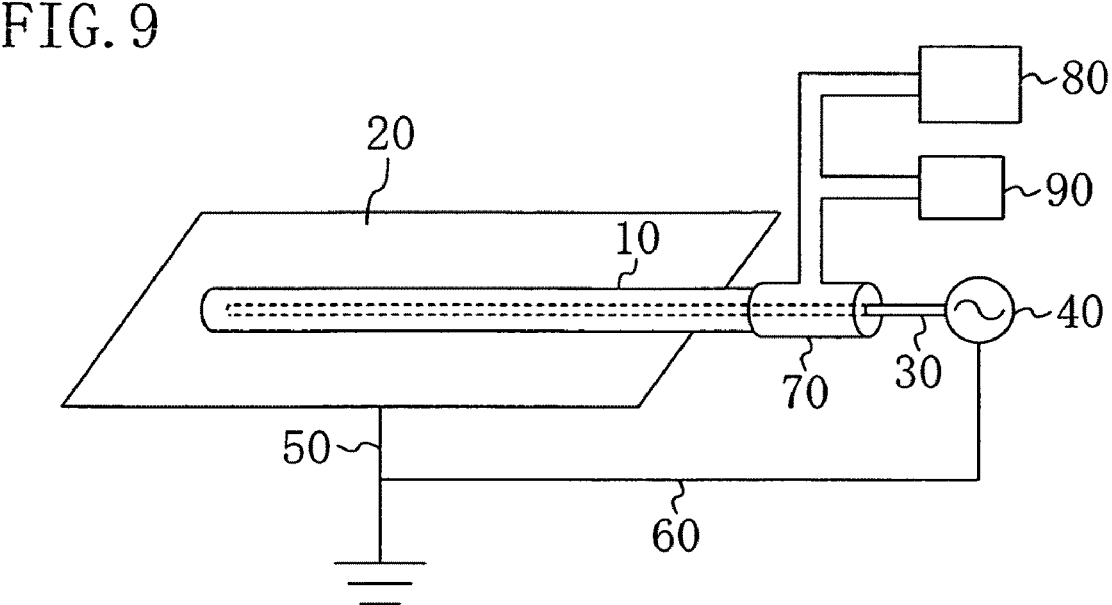
FIG. 9 is a schematic perspective view of a plasma generation system according to embodiment 4.
Figure 10:
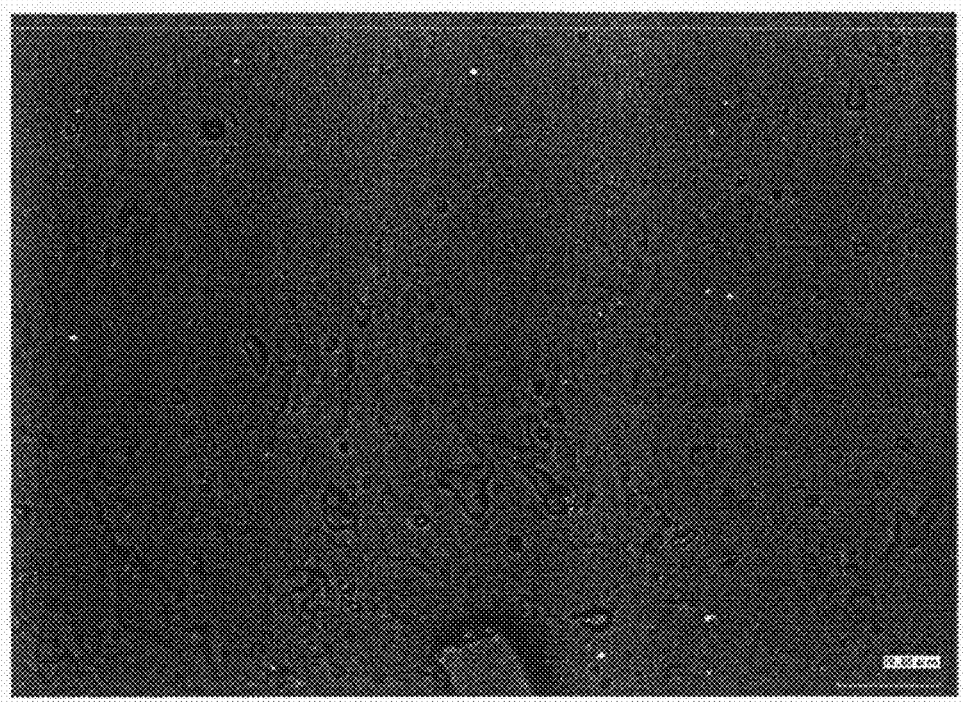
FIG. 10 is an enlarged picture image of a surface of a treated article according to Example 2.
Figure 11:
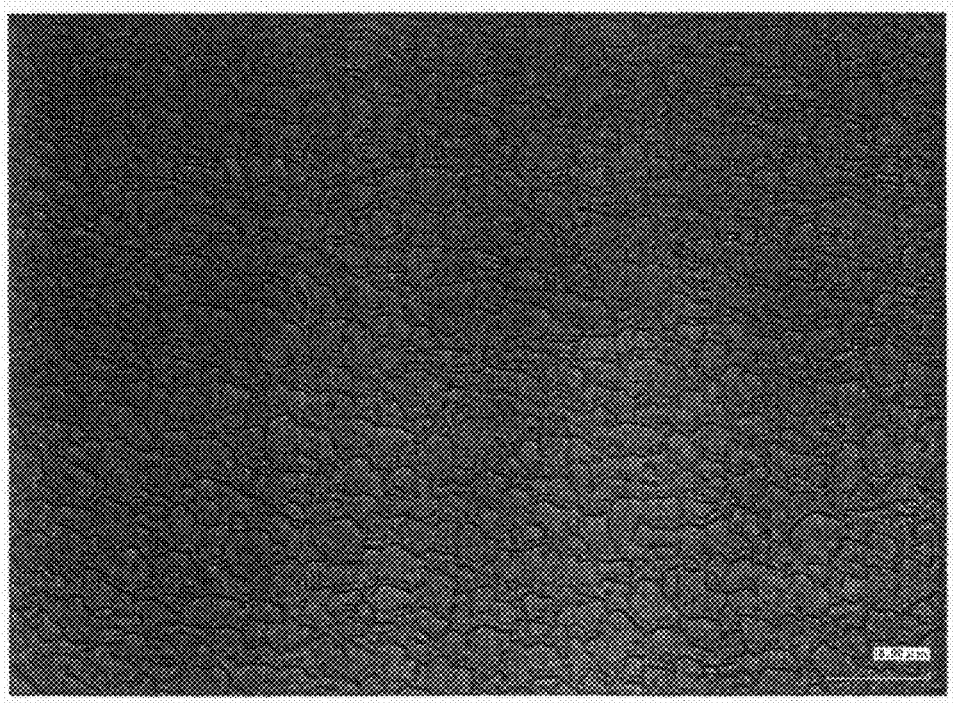
FIG. 11 is an enlarged picture image of a surface of an untreated article according to Example 2.
Figure 12:
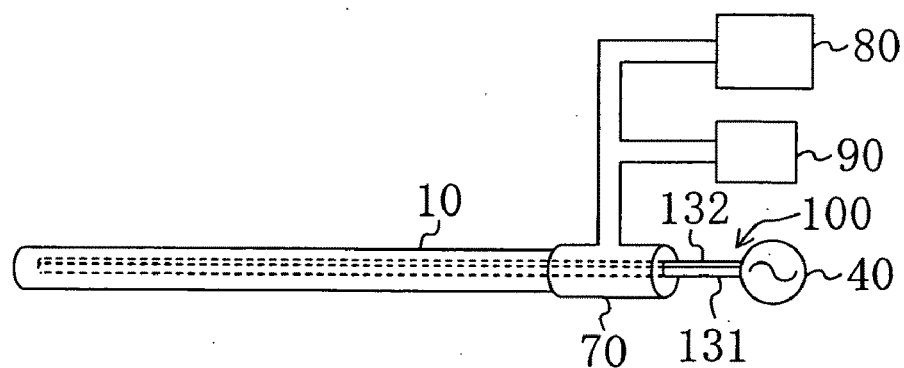
FIG. 12 is a schematic perspective view of a plasma generation system according to embodiment 6.
Figure 13:
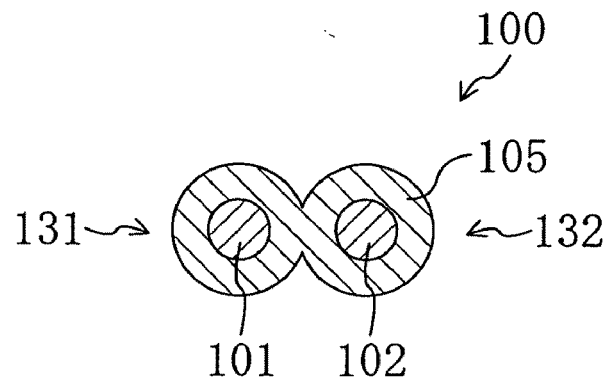
FIG. 13 is a cross-sectional view of a parallel electrode pair cable according to embodiment 6.
Figure 14:
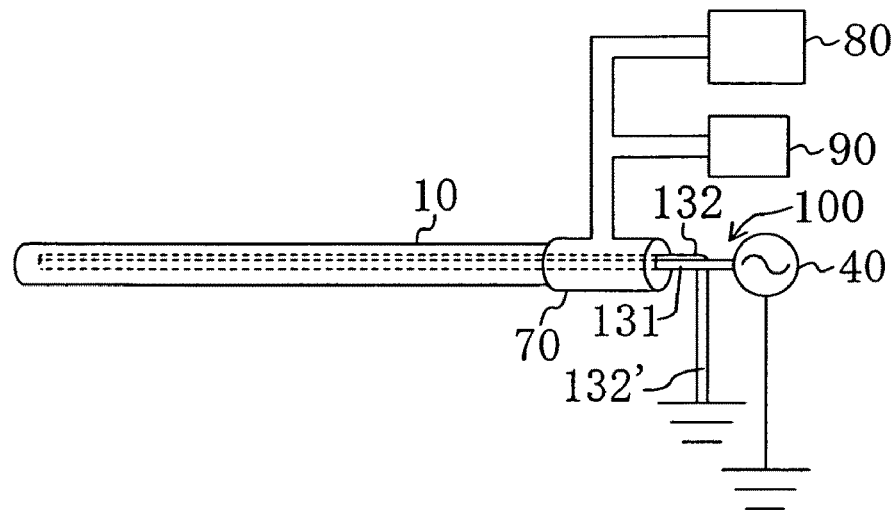
FIG. 14 is a schematic perspective view of a plasma generation system according to embodiment 7.
Figure 15:
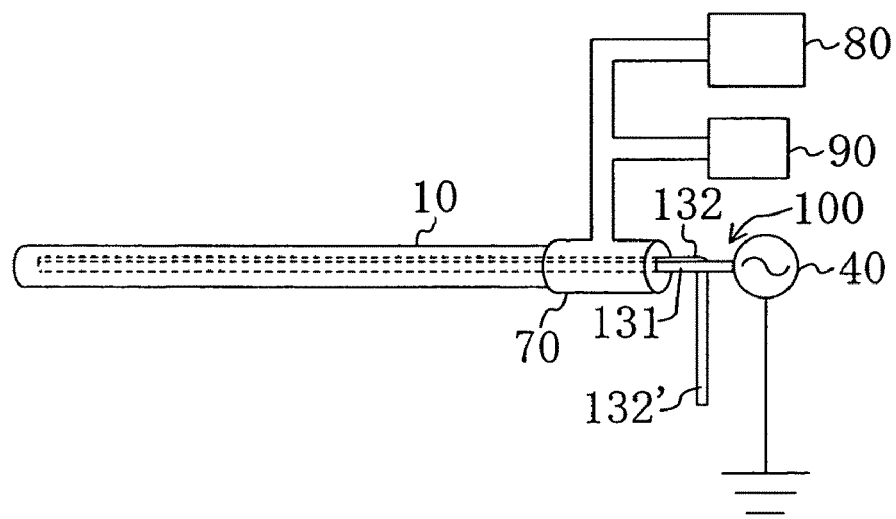
FIG. 15 is a schematic perspective view of a plasma generation system according to embodiment 8.
Figure 16:
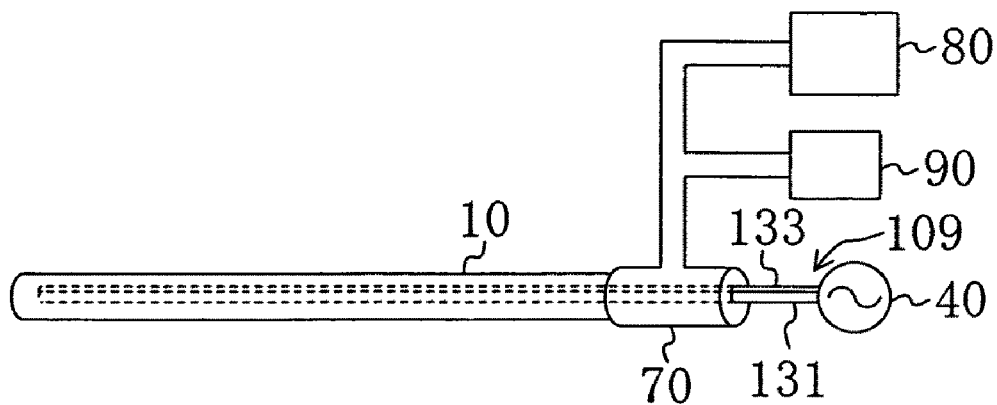
FIG. 16 is a schematic perspective view of a plasma generation system according to embodiment 9.
Figure 17:
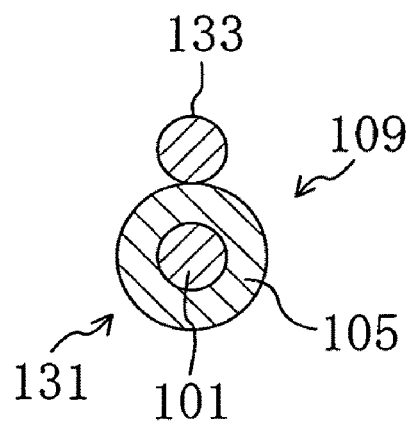
FIG. 17 is a cross-sectional view of a parallel electrode pair cable according to embodiment 9.
Figure 18:
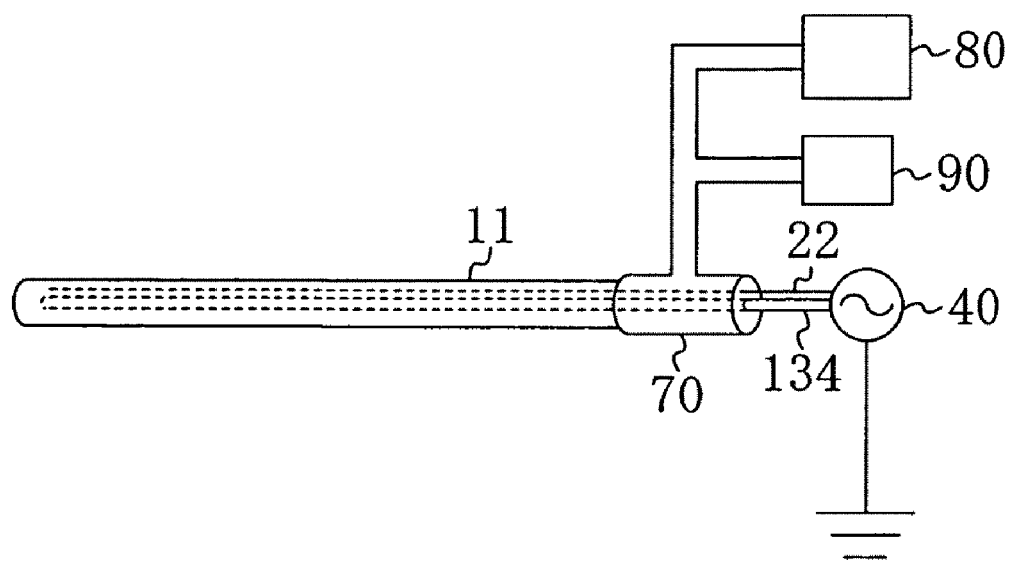
FIG. 18 is a schematic perspective view of a plasma generation system according to embodiment 10.

10, 11 narrow tube
20 second electrode
22 conductive element
30 first electrode
31 conductive member
32 clad
40 power supply
50 ground line
60, 65 connection line
70 adapter
80 gas supplier
90 gas remover
101 conductive member 102 conductive member
105 clad
131 first electrode
132 second electrode
133 second electrode
134 electrode

The invention claimed is:

1. A plasma generation system for generating plasma in a cavity of a narrow tube, comprising:
 a first electrode including a conductive member covered with an insulator or dielectric, the first electrode being inserted into the cavity of the narrow tube to generate the plasma;
 a power supply to apply an alternating voltage or pulse voltage to the first electrode; and
 a second electrode located in the cavity of the narrow tube, the second electrode being in an electrically floating state and being disconnected from the power supply, wherein
 the conductive member is made of a wire.

2. The plasma generation system of claim 1, wherein the second electrode includes a conductive member covered with an insulator or dielectric.

3. The plasma generation system of claim 1, further comprising a gas supplying member to flow a gas into the cavity of the narrow tube.

4. The plasma generation system of claim 1, further comprising a gas remover to remove a gas from the cavity of the narrow tube.

5. The plasma generation system of claim 1, wherein the plasma is used for a surface treatment on an inner wall of the narrow tube.

6. The plasma generation system of claim 1, wherein the plasma is used for sterilization of an inner wall of the narrow tube.

7. A plasma generation method for generating plasma in a cavity of a narrow tube, comprising:
 electrode inserting to insert into the cavity of the narrow tube a first electrode which includes a conductive member covered with an insulator or dielectric; and
 plasma generating to apply an alternating voltage or pulse voltage to the first electrode to generate plasma in the cavity of the narrow tube, wherein
 the conductive member is made of a wire, and
 the electrode inserting includes further inserting a second electrode which is in an electrically floating state into the cavity of the narrow tube and is disconnected from the power supply.

8. The plasma generation method of claim 7, wherein the plasma generating includes flowing a gas into the cavity of the narrow tube.

9. The plasma generation method of claim 7, further comprising flowing a gas into the cavity of the narrow tube after the plasma generating.

10. The plasma generation method of claim 7, further comprising removing a gas from the cavity of the narrow tube after the plasma generating.

11. The plasma generation method of claim 7, wherein the plasma generating includes using the plasma to perform a surface treatment on an inner wall of the narrow tube.

12. The plasma generation method of claim 7, wherein the plasma generating includes using the plasma to perform sterilization of an inner wall of the narrow tube.

* * * * *